United States Patent
Costecalde et al.

(10) Patent No.: US 8,157,838 B2
(45) Date of Patent: Apr. 17, 2012

(54) METHOD FOR DELIVERING AN OCCLUSION PLUG

(75) Inventors: Michel Costecalde, Montauban (FR); Jerome Cau, Poitiers (FR); Frederic Mouret, Nice (FR); Joachim Ramos Clamote, Nice (FR)

(73) Assignee: Protomed, Marseille (FR)

( * ) Notice: Subject to any disclaimer, the term of this patent is extended or adjusted under 35 U.S.C. 154(b) by 324 days.

(21) Appl. No.: 12/514,359

(22) PCT Filed: Nov. 7, 2007

(86) PCT No.: PCT/EP2007/062015
§ 371 (c)(1),
(2), (4) Date: May 11, 2009

(87) PCT Pub. No.: WO2008/058880
PCT Pub. Date: May 22, 2008

(65) Prior Publication Data
US 2010/0042145 A1     Feb. 18, 2010

(30) Foreign Application Priority Data
Nov. 14, 2006   (FR) ........................................ 0654900

(51) Int. Cl.
*A61B 17/08*     (2006.01)
(52) U.S. Cl. ...................................................... 606/213
(58) Field of Classification Search ............. 604/57–64, 604/11, 16–18, 187; 623/23.72; 606/213–217, 606/232, 151, 200, 108
See application file for complete search history.

(56) References Cited

U.S. PATENT DOCUMENTS

| | | | |
|---|---|---|---|
| 4,411,275 A * | 10/1983 | Raitto ........................... | 600/576 |
| 4,790,819 A | 12/1988 | Li et al. | |
| 5,326,350 A | 7/1994 | Li | |
| 6,086,607 A | 7/2000 | Cragg et al. | |
| 6,984,219 B2 * | 1/2006 | Ashby et al. .................... | 604/15 |
| 2005/0090860 A1 | 4/2005 | Paprocki | |
| 2005/0113737 A1* | 5/2005 | Ashby et al. .................... | 604/15 |
| 2006/0089667 A1* | 4/2006 | Ben-David .................... | 606/201 |

FOREIGN PATENT DOCUMENTS

| | | | |
|---|---|---|---|
| JP | 05084263 A | * | 4/1993 |
| WO | 94/26175 | | 11/1994 |
| WO | 96/22123 | | 7/1996 |
| WO | 00/19912 | | 4/2000 |

OTHER PUBLICATIONS

International Search Report dated Feb. 27, 2008, from corresponding PCT application.

* cited by examiner

*Primary Examiner* — Ryan Severson
*Assistant Examiner* — Rachel S Papeika
(74) *Attorney, Agent, or Firm* — Young & Thompson

(57) ABSTRACT

A device for delivering a plug (1) in a vessel of a human or animal body, includes an inserter provided with a guiding channel (4) and elements for urging the plug into the channel (4), characterized in that the channel (4) is adapted for radially compressing the plug during the displacement thereof towards the distal end of the channel (4). The compression of the plug (1) is carried out only a few seconds before its placement while respecting the integrity thereof. The elasticity characteristics of the plug (1) are thus fully preserved. The present device can be used in open surgery or endoscopy, mainly in vascular surgery.

17 Claims, 5 Drawing Sheets

Figure 12:
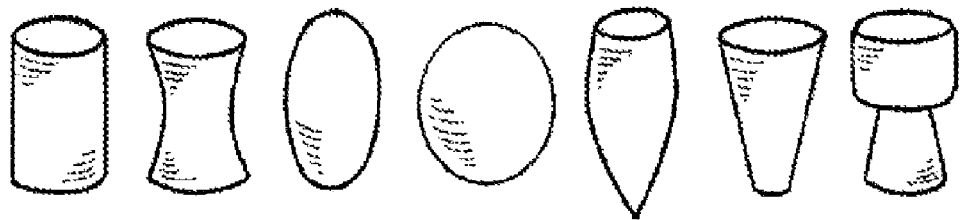

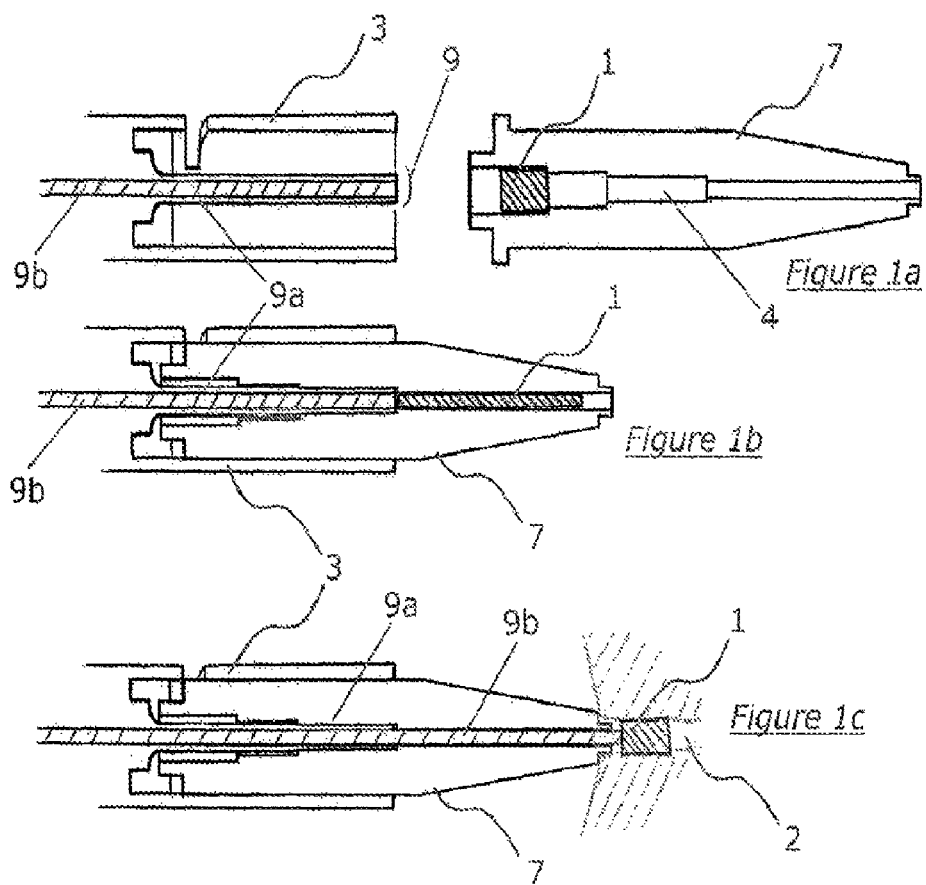
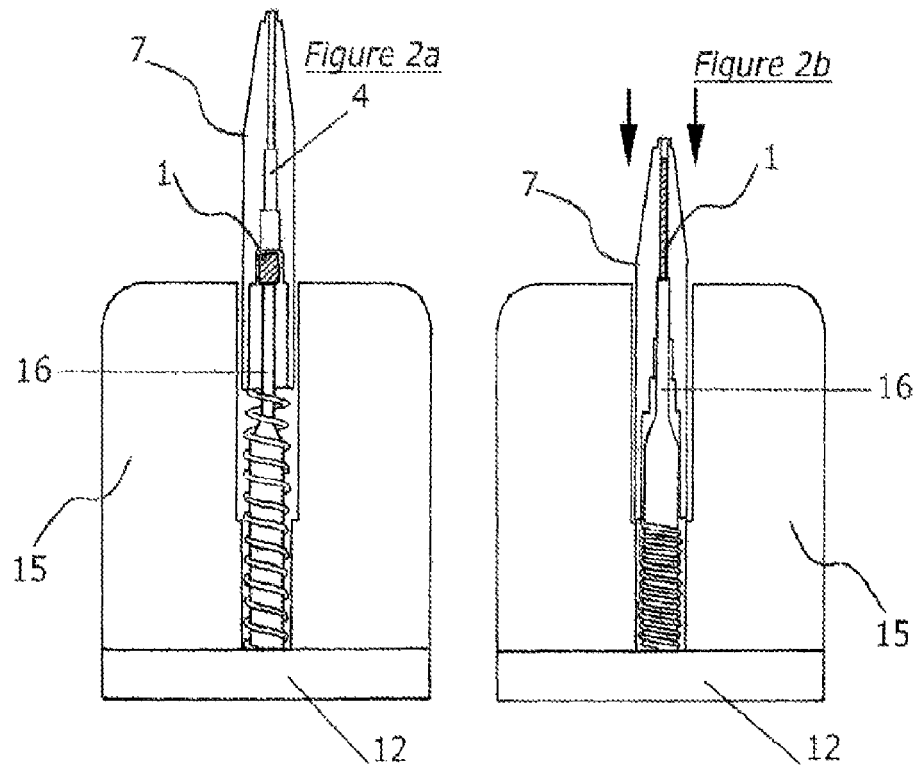

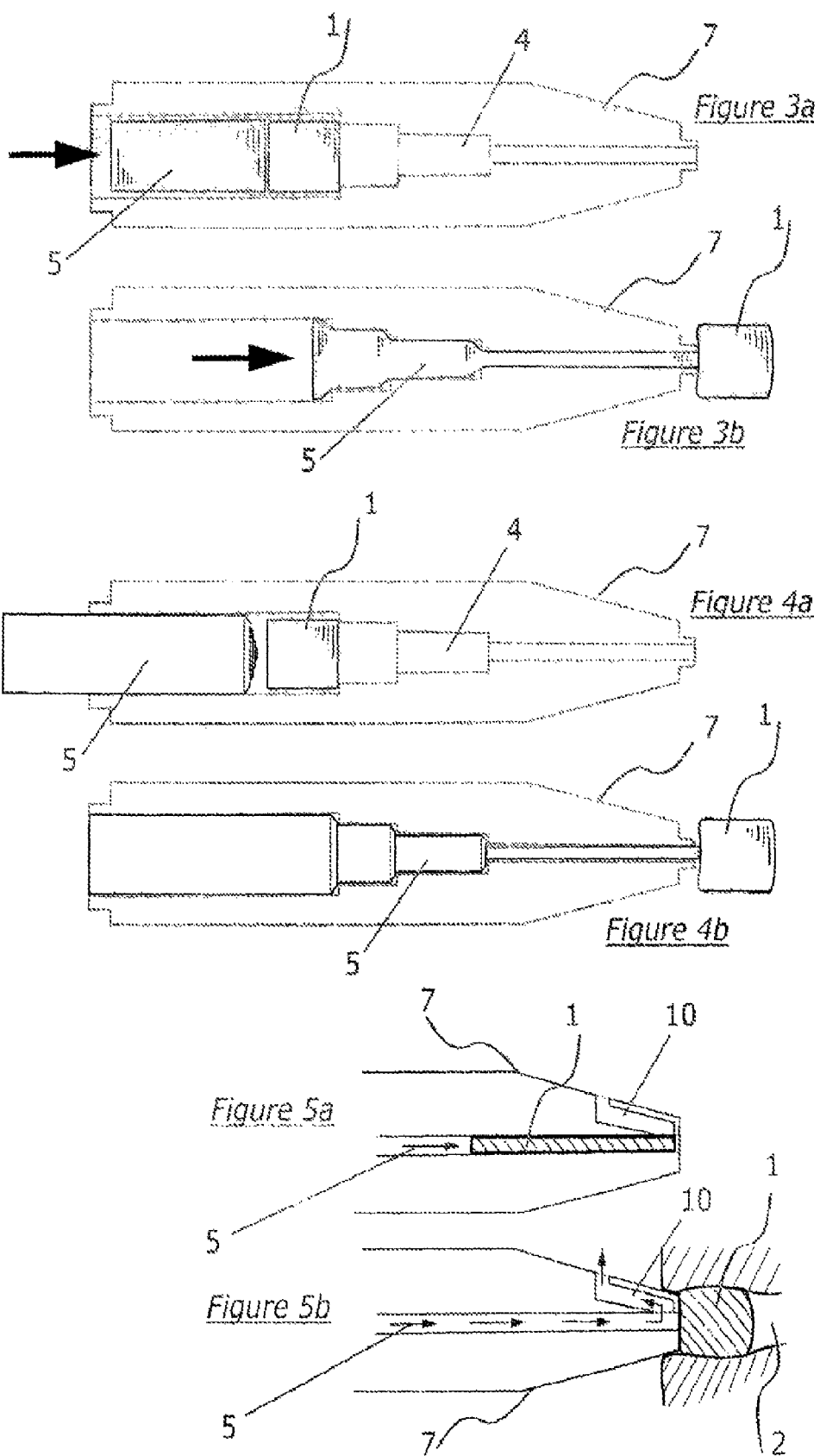

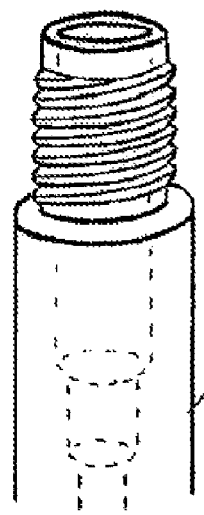
Figure 6
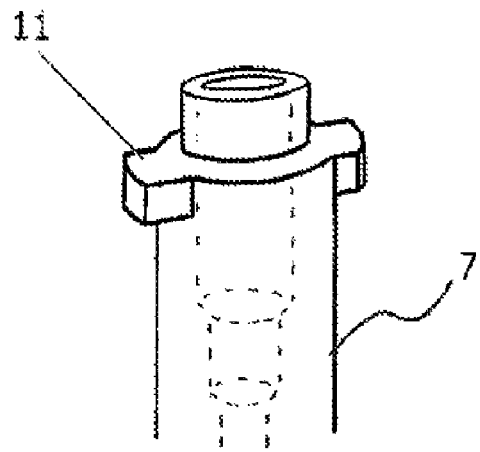
Figure 7
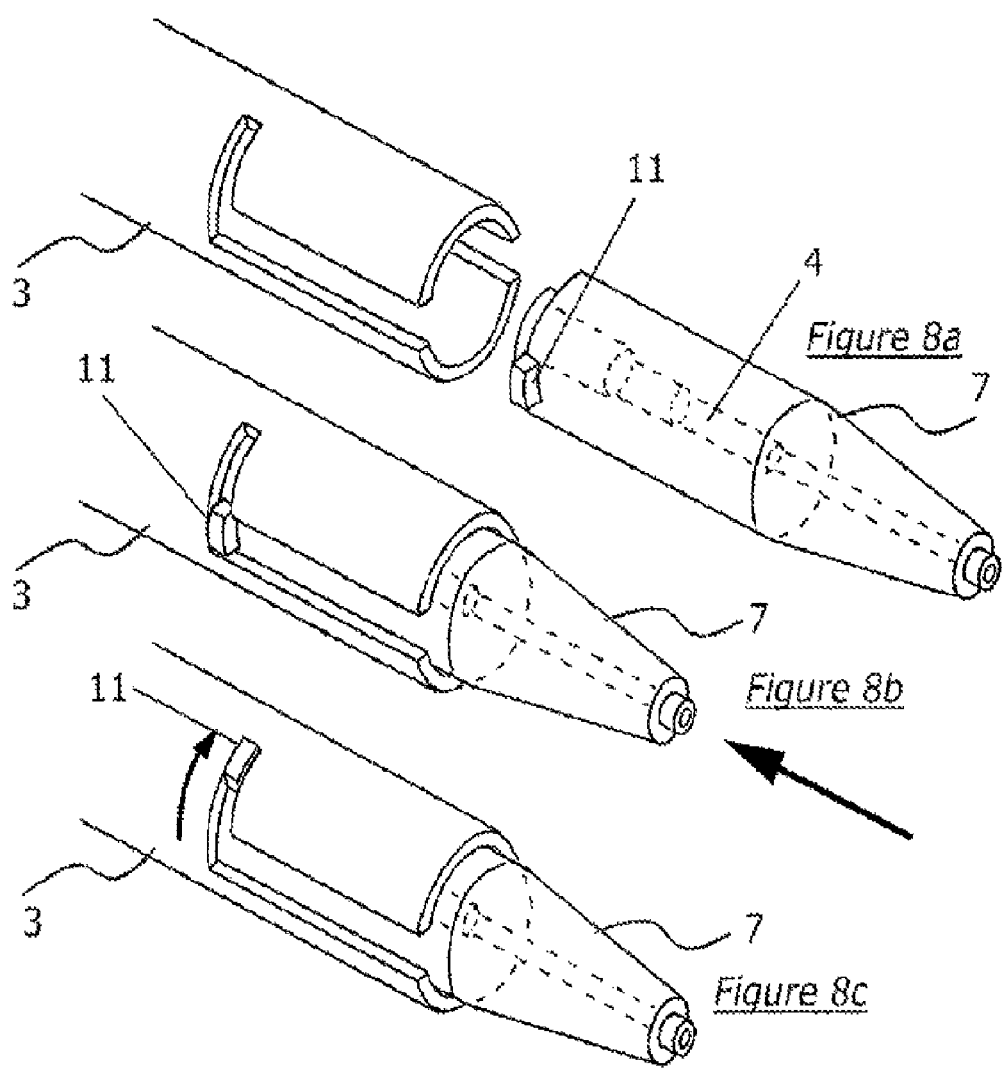
Figure 8a
Figure 8b
Figure 8c

METHOD FOR DELIVERING AN OCCLUSION PLUG

The present invention relates to a device for delivering a plug in a vessel of a human or animal body.

It applies particularly to vascular surgery for the occlusion of arteries such as lumbar, intercostal or other.

For example, reconstructive surgery for the aorta, especially following an abdominal aortic aneurysm, is a common operation, particularly in persons over 65 years of age. It represents 150,000 to 200,000 operations per year worldwide.

The technique consists of clamping the aneurysmal sac, opening it and removing the clot then replacing the aneurysm with a vascular prosthesis. There are five pairs of lumbar arteries in the posterior wall of the abdominal aorta. The lumbar arteries run along the lumbar vertebrae, dividing into two branches—a dorso-spinal (posterior) branch and an abdominal or intercostal lumbar (anterior branch).

During an operation on an aortic aneurysm, when the surgeon opens out the aneurysm, the lumbar arteries are exposed. They are then a source of a reflux of blood because it is open to the atmosphere. Reflux of blood occurs since it opens onto a low-pressure environment, unlike the network of arteries which is an environment under high pressure (relative pressure of the order of 100 mmhg). The blood flows back from a network of arteries on the periphery of the aorta which is clamped.

The conventional technique consists of tying off the lumbar arteries with a suture. While they are ligatured, the leaking arteries can be occluded digitally by surgical assistants or by clamping. Normally, only four to six arteries leak. The arteries remain tied after the operation because there is a peripheral network which takes over the circulation from these arteries. This loss of blood is a major feature of this type of surgery. Moreover, the time during which the aorta is clamped is critical for the patient. Any way of limiting this period and decreasing blood loss improves the post-operative outcome for the patient and allows for operations on patients in an even more serious condition.

The problem in conventional surgery becomes even more critical in laparoscopic surgery because it is impossible to occlude the arteries with digital pressure. Tying off is possible but difficult, requiring the surgeon to manipulate a needle using instruments within the abdomen. This takes precious time thereby considerably increasing blood loss (up to a liter of blood) and risk for the patient.

A number of solutions have been suggested to limit the time and difficulty involved in blocking off the lumbar arteries.

In most cases, an occlusion plug is used. The plug is compressed before being inserted in the vessel, returning to its original expanded form once in position.

It would not be possible to insert a compressed plug by deforming the vessels. The lumbar arteries have a small diameter, between 1 and 2.5 mm and their walls are thin and fragile. Dilation of the artery beyond its normal diameter in order to insert a plug may cause the artery to rupture, resulting in haemorrhage. Moreover, the arteries may be calcified, making them extremely rigid. It is therefore difficult to dilate them.

Document WO 0019912 describes a device for the occlusion of a transparietal perforation consisting of a compressed plug in an inserter consisting of an external constriction tube with a constant section and an internal slide mechanism. The plug is compressed when in the inserter. If the plug remains compressed for too long before being inserted, there is a risk of shape retention and it may not expand correctly.

Other documents present systems that are almost identical, for more complex uses. For example, document WO 94/26175 describes a device to insert an occlusion plug with an incurved tip in a blood vessel.

The various known devices consist of a single constriction mechanism holding the precompressed plug. The disadvantage of these devices is the risk of the plug not expanding correctly once inserted because of shape retention.

There is therefore a need for a device to insert an occlusion plug that will retain its elasticity.

To this end, the invention refers to a device to insert a plug into a vessel in a human or animal body, consisting of an inserter fitted with a guiding channel and the means of pushing the plug into the channel, characterised in that the said channel is configured to compress the plug radially as it is being moved towards the distal end of the channel and in that the means of pushing the plug consists of at least two imbricated rods sliding one into the other.

Compression is achieved just a few seconds before insertion, ensuring that the product retains all its characteristics. This ensures that the plug retains its full elasticity.

Advantageously, to compress the plug radially during its displacement towards the distal end of the channel, there is a succession of compartments of decreasing section or compartments according to another embodiment. The channel has a conical profile.

The plug is therefore pushed by a means of pushing, compressing the plug in the channel.

Advantageously, the channel lies at the distal end of said inserter in a movable tip. This type of design ensures that the device is either sterilisable or disposable.

According to one of the preferred embodiments of the invention, the device is such that:

the said channel consists of a succession of compartments of decreasing section.

the said channel is shaped like a truncated cone and is designed to decrease the section of the said channel towards its distal end.

the channel is located at the distal end of the said inserter at least partly in a movable tip.

the means for pushing the plug includes compression means located in a device to which the tip can be connected and terminal means for pushing located in the inserter.

the connection between the inserter and its movable tip consists of a bayonet fitting.

the connection between the inserter and its movable tip consists of a screw fitting.

one rod has a decreased section at its distal end.

the inserter is fitted with a spigot to make it easier to position the device in the vessel requiring occlusion the inserter is fitted, at its distal end, with an extended bearing surface to support the said device on the edge of the vessel requiring occlusion.

the means for pushing the plug includes an intermediate fluid to transmit stress from the imbricated rods to the plug.

the distal end of the said inserter is fitted with an outlet to avoid excess build-up of pressure.

said inserter includes a storage housing for the storage of plugs before use.

the storage housing includes a cylinder designed to store and distribute the plugs.

The invention also relates to a method to compress a plug characterised in that a delivery device is used as described previously and that the plug is introduced at the proximal end of a movable tip within the channel. The movable tip is connected to a device comprising a compression means and longitudinal pressure is exercised on the movable tip to introduce the compression means in the channel and push the plug towards the distal end of the channel where it undergoes an initial phase of radial compression. The movable tip is disconnected from the device and connected to an inserter with a terminal means for pushing including at least two rods imbricated one within the other. The terminal means for pushing is activated to push the plug towards the distal end of the channel where it undergoes a second phase of radial compression.

The enclosed drawings are given as examples and are not intended to limit the invention. They represent only one embodiment of the invention and make it easily understandable.

FIG. 1: Longitudinal section of the insertion device.
A. Movable tip not connected to the inserter.
B. Connection of the tip to the inserter.
C. Ejection of the plug.

FIG. 2: Longitudinal section according to one embodiment of the device designed to compress the plug and work with the movable tip.

FIG. 3: Longitudinal section of the device according to one embodiment in which the means for pushing are partly soft.

FIG. 4: Longitudinal section of the device according to one embodiment in which the means for pushing are rigid.

FIG. 5: Longitudinal section of the means of removal of the device according to one embodiment in which the means for pushing consist partly of fluid.

FIG. 6: Side view of the proximal end of the tip allowing the tip to be screwed onto the inserter.

FIG. 7: Side view of the proximal end of the movable tip allowing the tip to be mounted on the inserter by means of a bayonet fitting.

FIG. 8: Kinematic diagram showing the connection of the movable tip to the inserter by means of a bayonet fitting.

Figures 9, 10, 11:
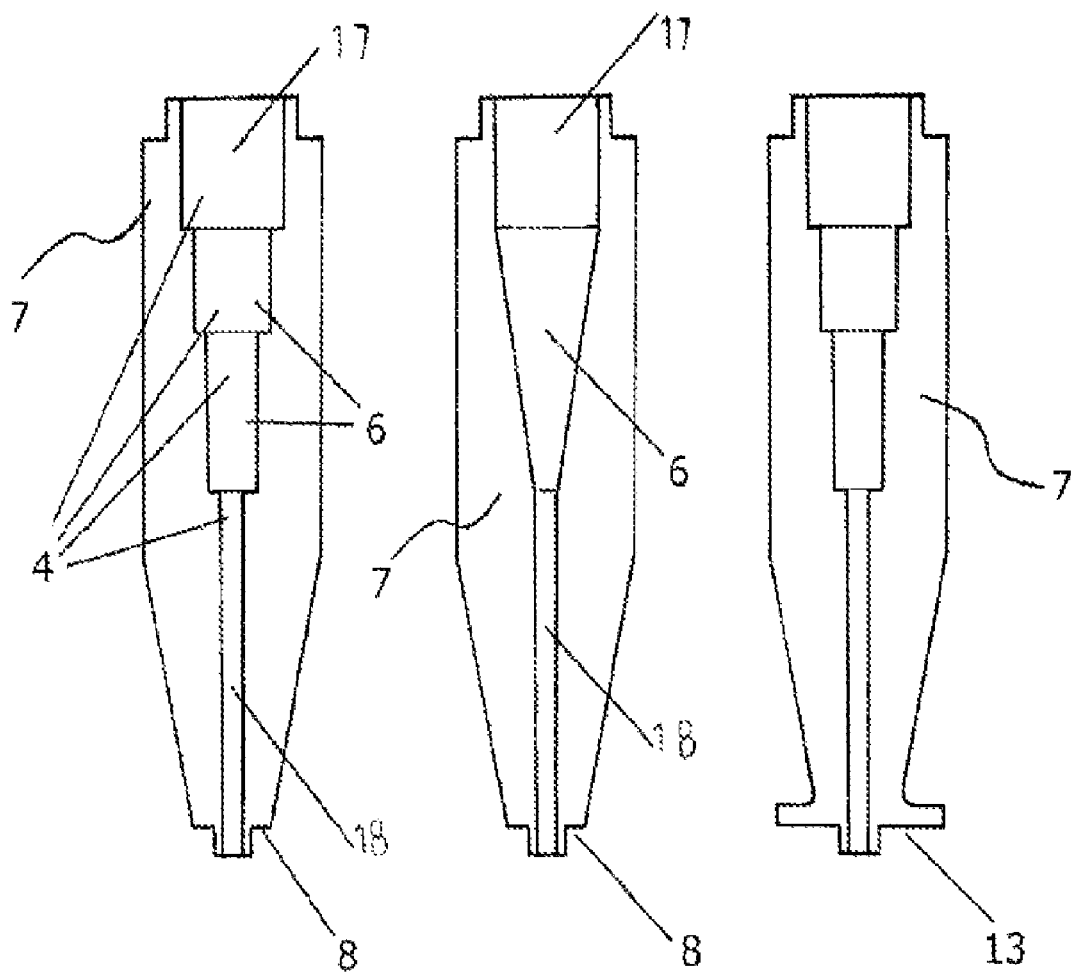

FIG. 9: Cross-section of the device according to one embodiment in which the guiding channel consists of a succession of compartments of decreasing section.

FIG. 10: Cross-section of the device according to one embodiment in which the guiding channel is conical in shape.

FIG. 11: Longitudinal section of the device having an enlarged support surface at its distal end.

FIG. 12: Presentation of the various possible shapes of the occlusion plug.

Figure 13:
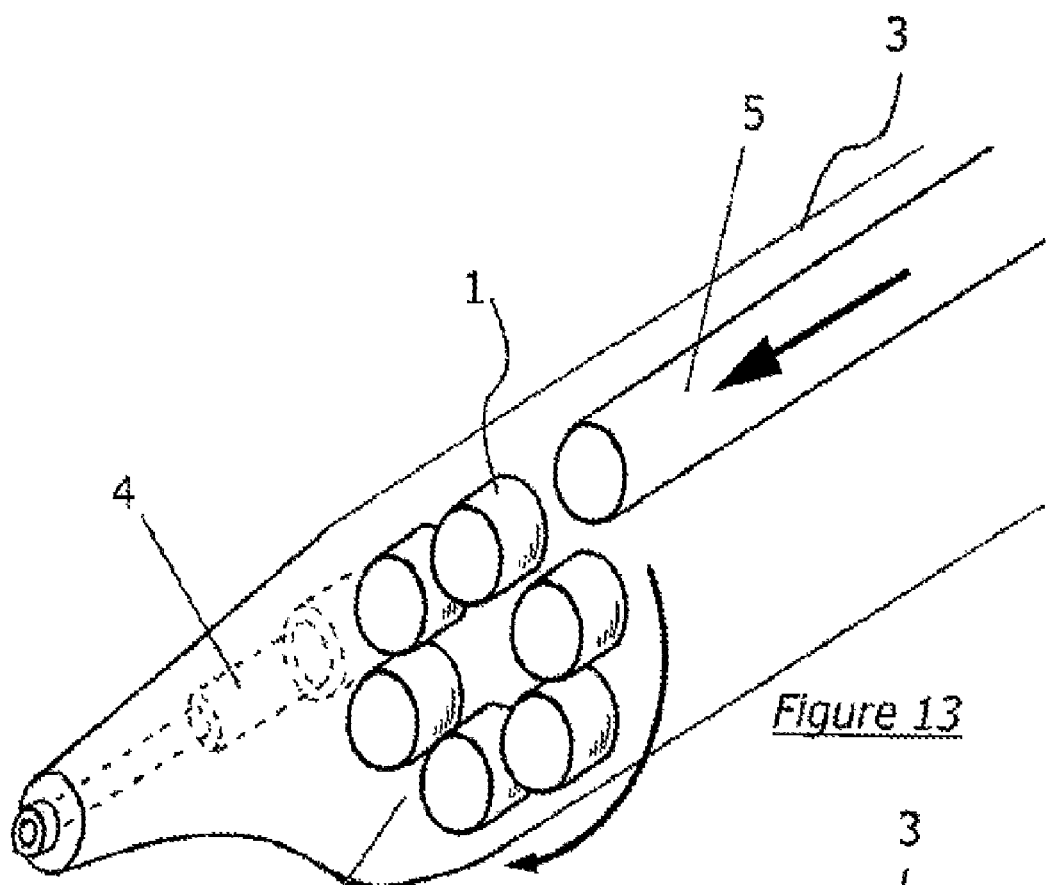

FIG. 13: View of the device according to one embodiment including a cylinder allowing the storage of several plugs.

Figure 14:
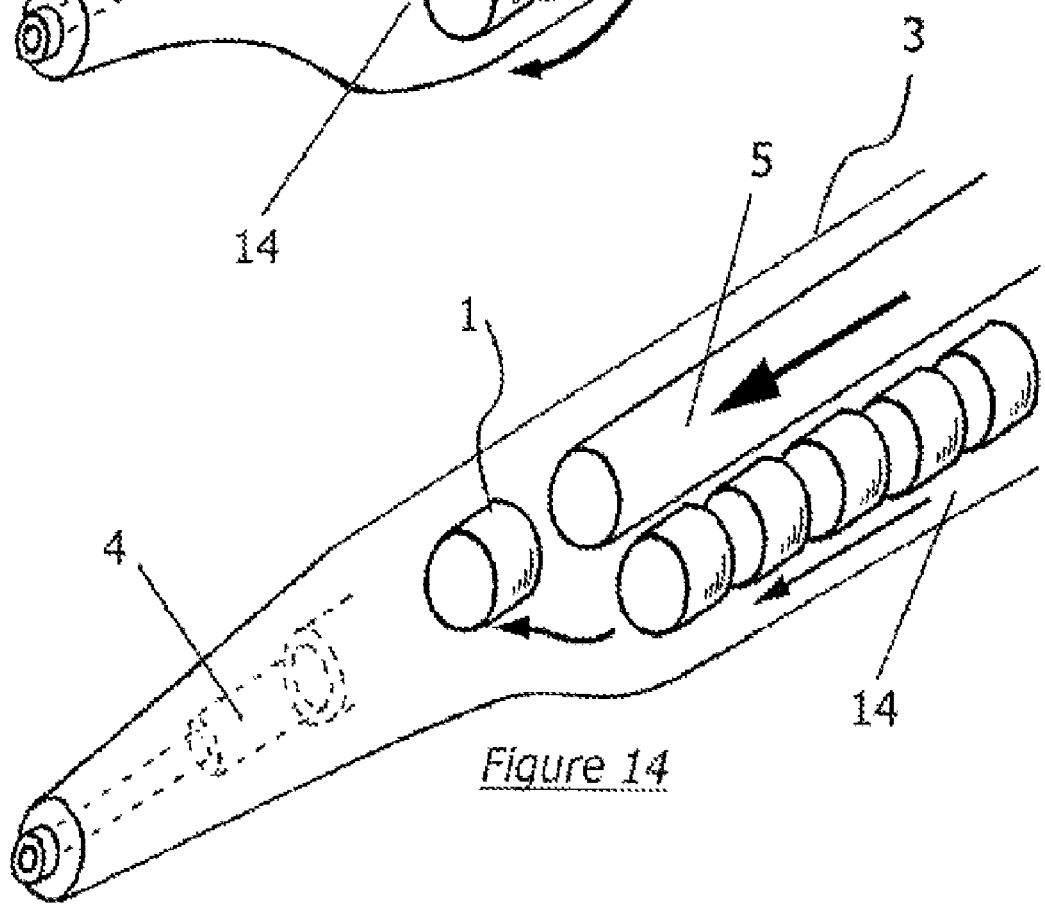

FIG. 14: View of the device showing housing used for the storage of plugs, one behind the other.

Other aims and advantages will become apparent during the description following the preferred embodiment of the invention which is, however, not limitative.

The present invention relates to a device for delivering a plug 1 into a vessel 2 in a human or animal body and consisting of an inserter 3 fitted with a guiding channel 4 and a mean pushing the plug 1 into the channel 4 characterised in that the said channel 4 is configured to compress the plug 1 radially during its displacement towards the distal end of channel 4.

Advantageously, the channel 4 consists of a succession of compartments 6, 17 and 18 with decreasing sections.

According to one embodiment, the last compartment has a section slightly smaller than the diameter of the vessel 2 requiring occlusion. Thus plug 1 is positioned in vessel 2 without damaging the walls.

Advantageously, the volume of each compartment is constant i.e. the sections of the compartments decrease in size while the length of each compartment increases.

According to another embodiment, the reduction in section can be continuous and be achieved, in particular, by means of a conical profile.

Advantageously, channel 4 lies at the distal end of the said inserter 3, at least partially in a movable tip 7.

Thus the insertion device can be sterilised and reused or be disposable after a single use or be a combination of both.

Channel 4 consists of three parts—an input compartment 17 for plug 1, an ejection compartment 18 for plug 1 and, between these two sections, a radial compression area 6. It is the passage from one compartment to the next through radial compression area that compresses the plug 1 radially.

Initially, the plug 1 is placed at the proximal end of the movable tip 7 in the input compartment 17, in a form only slightly compressed or totally non-compressed. Its insertion is therefore very practical.

According to FIG. 9, compression area 6 in channel 4 consists of a succession of compartments of decreasing section. The last compartment, ejection compartment 18, has the smallest section.

According to FIG. 10, compression area 6 of channel 4 consists of a tapered part.

According to one embodiment, the components used to push plug 1 exercise direct mechanical pressure on plug 1 so that it passes from input compartment 17 to ejection compartment 18 via radial compression area 6. The expression "direct mechanical pressure" means that the means for pushing come into contact with the rear of plug 1.

Depending on the configuration of channel 4, the means for pushing include a support section which decreases as the device is pushed.

According to a preferred embodiment, they consist of one or more solid rods 9 of decreasing section.

Moreover, the rods 9 are imbricated to produce a flat surface so that plug 1 is pushed with the largest possible support surface.

A rod 9 is displaced longitudinally along channel 4, pushing the plug 1 into the following compartment or into the tapered part. At this stage, the radially compressed plug 1 is located in the last, ejection compartment 18.

Advantageously, one of the rods 9 has a smaller section at its distal end.

Advantageously, the means for pushing have a support surface on plug 1 proportionate to the section of the plug. Thus the means for pushing do not damage plug 1.

To avoid the risk of damage to plug 1 by solid means for pushing coming into direct contact with plug 1, the device can be fitted with intermediate resources that act by indirect mechanical pressure. The expression "indirect mechanical pressure" means, for example, that the means for pushing are partly soft as shown in FIG. 3.

The partly soft means for pushing may be made from silicon or any other deformable material.

Thus the means for pushing include a soft material which transmits the push force generated by a fluid such as a gas or liquid or by a solid such as a rod or imbricated rods 9.

According to another embodiment including indirect mechanical pressure, the means for pushing include an intermediate fluid designed to transmit the stress from the imbricated rods 9 into the said plug 1.

The fluid used can be a liquid or a gas. It may or may not be compressible.

The advantage of this type of embodiment with an intermediate fluid is that it spreads the pressure from the devices uniformly, pushing against the entire rear surface of plug 1.

In this case, the means for pushing must be sealed to avoid any risk of fluid leakage and enable plug 1 to be pushed.

Thus a rod can be fitted, at its tip, with a seal.

The plug 1 must be compatible with the fluid i.e. the plug must not be damaged by the fluid and must be impervious to the fluid.

Advantageously, the said inserter 3 has an outlet 10 at its distal end to avoid a build-up of excess pressure. This outlet 10 consists, advantageously, of a threaded valve at a predetermined pressure placed in a pipe communicating at one end with channel 4 and at the other end with the exterior of the device.

According to another embodiment, the outlet 10 includes an aperture which opens when the piston is moved during compression of the plug 1.

The plug 1 has characteristics of radial and/or longitudinal expansion so that it is compressed while being moved towards the vessel requiring occlusion and, when released, it returns to an expanded form.

Advantageously, the plug 1 may be made of a biocompatible material of the polymer type, such as silicon, silicon foam, polyurethane, a hydrophilic material, a shape-memory polymer or a hydrogel. It may also be made of a biological type of material such as collagen or a metal such as stainless steel or a shape-memory alloy.

The plug 1 may have various shapes as represented in FIG. 12 e.g. cylindrical, bull-nosed, ovoid, spherical, the shape of a champagne cork, a T-shape, a truncated cone, a diabolo or an umbrella.

The said plug 1 may include means that makes it easier to maintain in vessel 2 (spigots, lugs, scales, striated lines etc.).

According to one embodiment, the plug 1 has a reinforced tip which is more resistant when pushed by means for pushing 5. The reinforced tip can be made by heat treatment or by a second material with a higher hardness rating.

The reinforced layer of plug 1 must be able to resist the stress of the means for pushing. For example, the layer may represent 1/10th of the total thickness of plug 1.

The reinforced layer, consisting of a more resistant material than the material used to make plug 1, may be added by gluing or by moulding it onto the said plug 1.

According to the embodiment in which the distal end of the said inserter 3 is a movable tip 7, advantageously the connection between the inserter 3 and its movable tip 7 consists of a bayonet fitting. The bayonet fitting consists of a slit at the distal end of the said inserter 3 into which are slotted the connection spigots 11 located on the proximal section of the movable tip 7 or inversely.

According to another embodiment, the connection between the inserter 3 and the said movable tip 7 is a screw connection.

Other means of connection can be used to connect the inserter 3 and the movable tip 7 such as clipping or any other fast-connection device.

The said delivery device is designed to insert the plug 1 into a vessel 2 of a human or animal body. It is therefore made of relatively hard material to withstand the compression stress of plug 1. The material of the inserter 3 may be metal or a polymer. It may or may not be transparent or may include a viewing window so that the ejection of plug 1 can be seen and monitored.

According to one embodiment, the inserter 3 is fitted with a spigot to make it easier to position the said device compared to vessel 2 requiring occlusion.

According to another embodiment, the said inserter 3 is fitted at its distal end with a bearing surface 8 to provide better support for the device round the edge of vessel 2 requiring occlusion.

Advantageously, the bearing surface 8 is an extended bearing surface 13 consisting of a larger diameter than the diameter of the end of the movable tip 7, thereby forming a support ring.

The advantage of this extended bearing surface 13 is that it allows control during insertion of the device in vessel 2 requiring occlusion.

In the cases described previously, the compression phase and final slide phase preceding the delivery of plug 1 are carried out successively within the inserter 3 by prolonged sliding of the plug 1 into channel 4. To achieve radial compression by direct mechanical pressure, this generally presupposes the imbrication of several slide pushing rods. Rods with decreasing sections are required to operate over the widest possible surface at the rear of plug 1 while passing successively through compartments of decreasing section or through a tapered part. A rod places the plug in compression and another rod, capable of longitudinal translation within the first rod, is used for the delivery of the plug 1.

According to another embodiment, the compression phase and final slide phase are not both carried out within the inserter but in two separate components.

The means for pushing the plug 1 include means of compression located in a device 15 that is separate from the inserter 3 and the final means for pushing 5 located in the inserter 3. The device 15 and the means of compression are able to work with the movable tip 7 to compress the plug 1 in the distal section of the said movable tip 7.

According to one embodiment, the said device 15 is a support 12 fitted with at least one rod 16 and, advantageously, two rods 9 imbricated one in the other able to work with the said movable tip 7 before its connection to the said inserter 3.

According to one embodiment, the imbricated rods 9 are located in device 15. In this case, the plug 1 is compressed in the channel 4 by activating the imbricated rods 9 in the device 15 then the movable tip 7 is mounted on the inserter 3 which includes at least one rod 9 designed to push the plug 1 out of the channel 4.

The movable tip 7 is placed upside down around the compression means. It rests against a return spring which pushes the movable tip 7 in the opposite direction to support 12.

If the movable tip 7 is connected to the inserter 3 by a bayonet fitting, the device 15 can work with the connection spigots 11 on the movable tip 7.

The spigots then also play a support role within device 15.

When the movable tip 7 is positioned on the device 15, it is blocked in rotation and cannot release itself. The only means of extracting it is to press on it and give it a quarter-turn so that the spigots on the movable tip 7 are released from their stop. During this movement, the plug 1 is transferred from the input compartment 17 to the compression zone or the ejection compartment 18 by the compression means.

The advantage of the device 15 is that the compression of the plug 1 is achieved only a few seconds before inserting it and the said plug 1 maintains its characteristics. This means that the plug 1 retains all its elasticity.

We will now describe a number of processes for the preparation of the said delivery device.

*According to one embodiment, the compression of the plug 1 is performed by the device 15 comprising compression means before the movable tip 7 is connected to the inserter 3.

The plug 1 is first inserted into the input compartment 17 at the proximal end of the said movable tip 7 which is then placed on the device 15 fitted with at least one rod 16. Longitudinal pressure on the said movable tip 7 introduces rod 16 of the compression means into channel 4 in the movable tip 7. The plug 1 is then pushed into the channel 4 where it is subjected to radial pressure.

At this point, the plug 1 is compressed in the distal end of the movable tip 7, in the ejection compartment 18. The movable tip is connected to the inserter 3 by various means of connection as described above.

By activating the terminal means of pushing 5, the plug 1 will be ejected from the device.

*According to another preferred embodiment illustrated in FIG. 1, plug 1 is compressed when the movable tip 7 is connected to the inserter 3.

When the movable tip 7, fitted with plug 1 at its proximal end, is mounted on the inserter 3 by various means of connection as described above, an immobile rod 9a in the inserter 3 presses on the plug 1 to move it into channel 4 towards the distal end of the said movable tip 7. This displacement causes the radial compression of the plug 1.

A mobile rod 9b on the inserter 3, imbricated in rod 9a, is then activated, pushing the plug 1 out of the device.

*According to another embodiment, the plug 1 is compressed after the connection of the movable tip 7 to the inserter 3. The movable tip 7 is connected to the inserter 3 by various means of connection described above.

The plug 1 is compressed by activating the means for pushing.

According to this embodiment, the means for pushing the plug 1 enables it to be compressed then ejected.

According to this embodiment, the two phases of compression and ejection can be achieved by a single activation of the means of pushing the plug 1 and by successive activation of the slide means.

The embodiments described above can be used separately or together.

According to one embodiment, the delivery device is an ancillary piece of equipment shaped like a conventional laparoscopy instrument. A trigger creates a movement of translation in a tie rod contained in a tube. When the trigger is pressed, the tie rod is displaced (translation of the proximal section of the tube towards the distal section).

Advantageously, the system can be lubricated with a viscous product or with a liquid to limit stress during compression and ejection.

According to one embodiment, a storage housing 14 can be in the body of the inserter 3. The storage housing 14 is used to store more than one plug 1 in the device, in a lightly compressed or uncompressed state.

The storage housing 14 may be cylindrical in shape. Rotation of the cylinder aligns the plug 1 with the means for pushing. The cylinder can be rotated manually by the practitioner or automatically as soon as the means for pushing are no longer aligned with the plug 1.

The storage housing 14 can also be longitudinal in shape to allow for the storage of plugs 1 in a line, one behind the other.

The means of advancing the plugs can be used to advance the plugs 1 and successively align one with the means of pushing.

REFERENCES

1. Plug
2. Blood vessel in the body
3. Inserter
4. Channel
5. Terminal means for pushing
6. Compression zone
7. Movable tip
8. Bearing surface
9. Rods 9a: immobile rod
   9b: mobile rod
10. Outlet
11. Connecting spigots
12. Support
13. Extended bearing surface
14. Storage housing
15. Device
16. Compression rod
17. Input compartment
18. Ejection compartment

The invention claimed is:

1. A device for delivering a plug (1) in a vessel (2) in a human or animal body, comprising:
   an inserter (3) fitted with a guiding channel (4) and a pushing device that pushes the plug (1) into the channel (4),
   wherein said channel (4) is configured to compress radially the plug (1) during the displacement thereof towards the distal end of the channel (4) and the pushing device comprises at least two telescopic rods (9) located in the channel, one of which slides in the other and each of the at least two telescopic rods exercising direct mechanical pressure on the plug.

2. The device according to claim 1, wherein said channel (4) consists of a succession of compartments of decreasing section.

3. The device according to claim 1, wherein said channel (4) is shaped like a truncated cone and is designed to decrease the section of the said channel (4) towards its distal end.

4. The device according claim 1, wherein the channel (4) is located at the distal end of the said inserter (3) at least partly in a movable tip (7).

5. The device according to claim 4, wherein the pushing device further comprises:
   a compression means located in a device (15) to which the moveable tip can be connected; and
   a terminal means for pushing (5) located in the inserter (3).

6. The device according to claim 4, wherein the connection between the inserter (3) and the movable tip (7) consists of a bayonet fitting.

7. The device according to claim 4, wherein the connection between the inserter (3) and its movable tip (7) consists of a screw fitting.

8. The device according to claim 1, wherein one rod (9) of the at least two telescopic rods has a decreased section at the one rod's distal end.

9. The device according to claim 1, wherein the inserter (3) is fitted with a projection to make it easier to position the device in the vessel requiring occlusion.

10. The device according to claim 1, wherein the inserter (3) has at a distal end, an extended bearing surface (13) to support the said device on the edge of the vessel requiring occlusion (2).

11. The device according to claim 1, wherein said inserter (3) includes a storage housing (14) for the storage of plugs (1) before use.

12. The device according to claim 11, wherein the storage housing (14) includes a cylinder designed to store and distribute the plugs (1).

13. The device according to claim 1, wherein the pushing device includes an intermediate fluid to transmit stress from the at least two telescopic rods (9) to the plug (1).

14. The device according to claim 13, wherein the distal end of the said inserter (3) contains an outlet (10) to avoid excess build-up of pressure.

15. A method for compressing a plug (1) of a device for delivering the plug (1) in a vessel (2) in a human or animal body, with an inserter (3) fitted with a guiding channel (4) and a pushing device that pushes the plug (1) into the channel (4), wherein said channel (4) is configured to compress radially the plug (1) during the displacement thereof towards the distal end of the channel (4) and the pushing device comprises at least two telescopic rods (9) located in the channel, one of which slides in the other and each of the at least two telescopic rods exercising direct mechanical pressure on the plug, the method comprising:

introducing the plug (1) at the proximal end of a movable tip (7) into a channel (4);

connecting the movable tip (7) to a device (15) comprising compression means;

exercising longitudinal pressure on the movable tip (7) to introduce the compression means into the channel (4) and push the plug (1) towards the distal end of the channel (4);

disconnecting the movable tip (7) from the device (15);

connecting the movable tip (7) to an inserter (3) comprising terminal means for pushing (5); and activating the terminal means for pushing (5) to displace the plug (1) towards the distal end of channel (4).

16. The device according to claim 5, wherein the connection between the inserter (3) and its movable tip (7) consists of a bayonet fitting.

17. The device according to claim 5, wherein the connection between the inserter (3) and its movable tip (7) consists of a screw fitting.

* * * * *